US008710288B2

(12) United States Patent
Liu et al.

(10) Patent No.: US 8,710,288 B2
(45) Date of Patent: Apr. 29, 2014

(54) PROCESS TO INCREASE SELECTIVITY TO ETHYLENE IN OXYGENATES-TO-OLEFINS CONVERSIONS

(75) Inventors: Yu Liu, Lake Jackson, TX (US); Albert E. Schweizer, Jr., Port St. Lucie, FL (US); Andrzej M. Malek, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/576,429

(22) PCT Filed: Mar. 11, 2011

(86) PCT No.: PCT/US2011/028017
§ 371 (c)(1),
(2), (4) Date: Aug. 1, 2012

(87) PCT Pub. No.: WO2011/126664
PCT Pub. Date: Oct. 13, 2011

(65) Prior Publication Data
US 2013/0012748 A1 Jan. 10, 2013

Related U.S. Application Data

(60) Provisional application No. 61/319,307, filed on Mar. 31, 2010.

(51) Int. Cl.
*C07C 1/20* (2006.01)

(52) U.S. Cl.
USPC .............................. 585/639; 585/640; 585/638

(58) Field of Classification Search
USPC ............ 585/638, 639, 640, 641, 642; 502/60, 502/61, 62, 63, 64, 208, 209, 210, 211, 212, 502/213, 214
See application file for complete search history.

(56) References Cited

U.S. PATENT DOCUMENTS

| | | |
|---|---|---|
| 4,076,796 A | 2/1978 | Reh et al. |
| 4,440,871 A | 4/1984 | Lok et al. |
| 5,279,810 A | 1/1994 | Calabro |
| 6,166,282 A | 12/2000 | Miller |
| 6,287,522 B1 | 9/2001 | Lomas |
| 6,518,475 B2 | 2/2003 | Fung et al. |
| 7,057,083 B2 | 6/2006 | Xu et al. |
| 2005/0101817 A1 | 5/2005 | Xu et al. |
| 2005/0148462 A1 | 7/2005 | Mees et al. |
| 2007/0100186 A1 | 5/2007 | Gao et al. |

OTHER PUBLICATIONS

Barger, Proceedings of the 12th Internationa Zeolite Conference 1(1999)567.
Chen, "Catalysis Letters", vol. 28, pp. 241-248 (1994).
Chen, "Journal of Physical Chemistry", vol. 98, pp. 10216-10224 (1994).
Chen, "Studies in Surface Science and Catalysis", vol. 84, pp. 1731-1738.
INUI, Appl. Catal. 164(1997)211.
Prakash, "Journal of the Chemical Society, Faraday Transactions," vol. 90(15), pp. 2291-2296 (1994).
Song, Angew. Chem. Int.Ed. 42(2003)892.
Wu, Appl. Catal. 260(2004)63.
Xu, "Journal of the Chemical Society, Faraday Transactions," vol. 86(2), pp. 425-429 (1990).
Zenz, Riser Reactor, Fluidization and Fluid-Particle Systems, pp. 48-59 (Reinhold Publishing Corporation, New York 1960).
PCT/US2011/028017, International Search Report and Written Opinion.
PCT/US2011/028017, International Preliminary Report on Patentability.

*Primary Examiner* — In Suk Bullock
*Assistant Examiner* — Sharon Pregler

(57) ABSTRACT

A process for converting an oxygenate-containing feedstock to a product comprising olefins comprises including in the oxygenate-containing feedstock an amount of ammonia. The presence of the ammonia increases the product's ratio of ethylene to propylene.

5 Claims, No Drawings

PROCESS TO INCREASE SELECTIVITY TO ETHYLENE IN OXYGENATES-TO-OLEFINS CONVERSIONS

This application is a non-provisional application claiming priority from the U.S. Provisional Patent Application No. 61/319,307, filed on Mar. 31, 2010, entitled "PROCESS TO INCREASE SELECTIVITY TO ETHYLENE IN OXYGENATES-TO-OLEFINS CONVERSIONS" the teachings of which are incorporated by reference herein, as if reproduced in full hereinbelow.

BACKGROUND

1. Field of the Invention

The invention relates to processes for converting oxygenates to olefins, particularly to ethylene and propylene. More particularly, the invention relates to processes wherein the ratio of ethylene to propylene is increased.

2. Background of the Art

Light olefins, such as ethylene, propylene, butylenes and mixtures thereof, serve as feeds for the production of numerous important chemicals and polymers. Typically, $C_2$-$C_4$ light olefins are produced by cracking petroleum refinery streams, such as $C_{3+}$ paraffinic feeds. In view of limited supply of competitive petroleum feeds, production of low cost light olefins from petroleum feeds is subject to waning supplies. Efforts to develop light olefin production technologies based on alternative feeds have therefore increased.

An important type of alternative feed for the production of light olefins is oxygenates, such as $C_1$-$C_4$ alkanols, especially methanol and ethanol; $C_2$-$C_4$ dialkyl ethers, especially dimethyl ether (DME), methyl ethyl ether and diethyl ether; dimethyl carbonate and methyl formate, and mixtures thereof. Many of these oxygenates may be produced from alternative sources by fermentation, or from synthesis gas derived from natural gas, petroleum liquids, carbonaceous materials, including coal, recycled plastic, municipal waste, or any organic material. Because of the wide variety of sources, alcohol, alcohol derivatives, and other oxygenates have promise as an economical, non-petroleum sources for light olefin production.

The preferred process for converting an oxygenate feedstock, such as methanol or dimethyl ether (DME), into one or more olefins involves contacting the feedstock with a crystalline molecular sieve catalyst composition. Variations in this process have included increasing reaction temperature, adjusting dilution level, modifying the crystalline molecular sieve catalyst composition, and pretreating the molecular sieve with an oxygenate or an olefin. These modifications are intended to increase yield and/or alter selectivity toward particular end products.

In spite of many technological advances in converting oxygenates to olefins, however, there remains a need to further increase the quantity of light olefins in the conversion product. In particular, there remains a need to increase product selectivity to ethylene and propylene, and particularly to ethylene.

SUMMARY OF THE INVENTION

In one embodiment the invention provides a process for converting an oxygenate-containing feedstock to a product comprising olefins, the process comprising including in the oxygenate-containing feedstock at least 0.01 percent by weight of ammonia, under oxygenate- to -olefin conversion conditions.

In another embodiment the invention provides a process for converting methanol to olefins comprising passing a methanol feed over a catalyst capable of converting methanol to a product including ethylene and propylene, wherein from 0.05 to 0.5 weight percent of ammonia is included in the methanol feed, such that the ratio of ethylene to propylene in the product is increased in comparison with the product of a process that is otherwise identical but lacks ammonia.

DETAILED DESCRIPTION OF THE EMBODIMENTS

As previously stated, the process of the invention is particularly intended for use in the conversion of organic oxygenates to olefins. The process may significantly increase (by as much as 15 percent by weight, preferably at least 5 percent, and more preferably at least 10 percent) the ratio of ethylene to propylene, which therefore may represent a significant increase (by as much as 3 to 4 percent by weight, preferably at least 2 percent by weight) in the selectivity to ethylene, even where the selectivity to ethylene plus propylene (combined) may not be increased.

Representative organic oxygenates useful in the invention include lower straight chain or branched aliphatic alcohols and their unsaturated counterparts. Examples of suitable oxygenate compounds include methanol; ethanol; n-propanol; isopropanol; $C_4$-$C_{10}$ alcohols; methyl ethyl ether; dimethyl ether; diethyl ether; diisopropyl ether; and combinations thereof. Particularly suitable oxygenate compounds are methanol, dimethyl ether, and combinations thereof, most preferably methanol. As used herein, the term "oxygenate" designates only the organic material used as the feed.

Particularly important to the present invention is the inclusion in the feed of a small amount of ammonia, which serves to increase the overall selectivity of the conversion process to ethylene and/or propylene. Desirably the ammonia is present in the feed in an amount of from 0.05 percent by weight to 0.5 percent by weight, based on the weight of the oxygenate.

In some embodiments one or more the diluents may be employed to assist the process flow. Such diluent may be generally non-reactive to both the feedstock and, if employed, catalyst, and may be used to reduce the concentration of oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. The diluent(s) may comprise from 1 mole percent (mol %) to 99 mol % of the total feed mixture.

In the inventive oxygenate conversion process, a feedstock comprising the selected organic oxygenate, optionally with one or more diluents, and the ammonia is contacted in the vapor phase in a reaction zone with a catalyst suitable to convert the selected oxygenate to olefins under conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result, depending upon the catalyst and the reaction conditions.

Any catalyst capable of converting the selected organic oxygenate to olefin may be used in this invention. Molecular sieve catalysts are preferred. Molecular sieves have been classified by the Structure Commission of the International Zeolite Association according to the rules of the IUPAC Commission on Zeolite Nomenclature. According to this classification, framework-type zeolite and zeolite-type molecular sieves, for which a structure has been established, are assigned a three letter code and are described in the Atlas of Zeolite Framework Types, 5th edition, Elsevier, London, England (2001), which is herein fully incorporated by reference.

Examples of suitable catalysts may include zeolite as well as non-zeolite molecular sieves, and may be of the large, medium or small pore type. Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Thus, molecular sieves may have from a 4-ring to a 12-ring or greater framework-type. In a preferred embodiment, the molecular sieves used in the invention have 8-, 10- or 12-ring structures and/or an average pore size in the range of from 3 Angstroms (Å) to 15 Å. In the most preferred embodiment, the molecular sieves preferably have an 8-ring framework and an average pore size less than 5 Å, preferably ranging from 3 Å to 5 Å, more preferably from 3 Å to 4.5 Å, and most preferably from 3.5 Å to 4.2 Å.

Other framework-type characteristics include the arrangement of rings that form a cage, and when present, the dimension of channels, and the spaces between the cages. See van Bekkum, et al., *Introduction to Zeolite Science and Practice*, Second Completely Revised and Expanded Edition, Vol. 137, pp. 1-67 (Elsevier Science, B.V., Amsterdam, Netherlands 2001). Non-limiting examples of suitable molecular sieves are the small pore molecular sieves that are designated as having either AEI or CHA topology, or a combination thereof. In one preferred embodiment, the molecular sieve used in the inventive process has a CHA topology. Preferably their frameworks are silicoaluminophosphate or aluminophosphate. Thus, their type may be designated as, respectively, SAPO or ALPO molecular sieves. Such may be substituted with additional atoms, preferably metals. In one embodiment, the substituted metal may be an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as $[MeO_2]$, and carry a net charge depending on the valence state of the metal substituent. For example, in one embodiment, when the metal substituent has a valence state of +2, +3, +4, +5, or +6, the net charge of the tetrahedral unit is between −2 and +2. In some cases water may form a part of the crystal frameworks, and these molecular sieves are designated as the corresponding hydrates.

The most preferred molecular sieves are SAPO molecular sieves and metal-substituted SAPO molecular sieves.

Non-limiting examples of SAPO and ALPO molecular sieves used in the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal substituted molecular sieves corresponding thereto. For example, SAPO-34 is a crystalline silicoaluminophosphate molecular sieve of the CHA framework type and has been found to exhibit relatively high product selectivity to ethylene and propylene, and low product selectivity to paraffins and olefins with four or more carbon atoms.

The preparation and characterization of SAPO-34 has been reported in several publications, including U.S. Pat. No. 4,440,871; J. Chen et al. in "Studies in Surface Science and Catalysis", Vol. 84, pp. 1731-1738; U.S. Pat. No. 5,279,810; J. Chen et al. in "Journal of Physical Chemistry", Vol. 98, pp. 10216-10224 (1994); J. Chen et al. in "Catalysis Letters", Vol. 28, pp. 241-248 (1994); A. M. Prakash et al. in "Journal of the Chemical Society, Faraday Transactions," Vol. 90(15), pp. 2291-2296 (1994); Yan Xu et al. in "Journal of the Chemical Society, Faraday Transactions," Vol. 86(2), pp. 425-429 (1990). These silicon-, aluminum-, and phosphorus-based molecular sieves, and metal containing silicon-, aluminum- and phosphorus-based molecular sieves, have been described in detail in numerous other publications and patents, and will be generally familiar to and understood by the skilled practitioner.

The process for converting the oxygenate feedstock is, preferably, a continuous fluidized bed process, and most preferably a continuous fluidized bed process. The reaction process can be carried out using a variety of types of catalytic reactors, including but not limited to hybrid reactors that have a dense bed or fixed bed reaction zones and/or fast fluidized bed reaction zones coupled together; circulating fluidized bed reactors; and riser reactors. Suitable conventional reactor types are described in, for example, U.S. Pat. Nos. 4,076,796, 6,287,522 (dual riser), and Kunii, et al., *Fluidization Engineering* (Robert E. Krieger Publishing Company, New York 1977), which are both herein fully incorporated by reference.

One applicable reactor type is a riser reactor. This type of reactor is generally described in, for example, Zenz, et al., *Riser Reactor, Fluidization and Fluid-Particle Systems*, pp. 48-59 (Reinhold Publishing Corporation, New York 1960), and U.S. Pat. No. 6,166,282 (fast-fluidized bed reactor), which are both herein fully incorporated by reference.

In one embodiment of the invention, a fluidized bed process includes a reactor system, catalyst separation system, and a regeneration system. The reactor system is preferably a fluid bed reactor system. In one embodiment, the fluid bed reactor system has a first reaction zone within one or more riser reactors, and a second reaction zone within at least one catalyst separation vessel, preferably comprising one or more cyclones. In one embodiment, one or more riser reactors and a catalyst separation vessel is contained within a single reactor vessel.

In the inventive process an oxygenate-containing feedstock, preferably containing one or more oxygenates, and optionally one or more diluents, is fed to a reactor wherein a suitable catalyst composition, preferably a molecular sieve catalyst composition, is introduced. In one embodiment, the molecular sieve catalyst composition is contacted with a liquid or gas, or combination thereof, prior to being introduced to the reactor. Preferably, the liquid is water or methanol, and the gas is an inert gas such as nitrogen.

Reaction conditions include any conditions that are useful for oxygenate-to-olefin conversions. Such may include a reactor temperature within a wide range, preferably from 200 degrees Celsius (° C.) to 1000° C., more preferably from 200° C. to 800° C., still more preferably from 200° C. to 700° C., and yet still more preferably from 300° C. to 650° C. In certain embodiments a range from 350° C. to 600° C., and most preferably from 400° C. to 600° C., is selected. Suitable pressures for the reaction may also vary greatly, and may include, for example, pressures preferably ranging from 0.01 megapascals (MPa) to 2 MPa. The foregoing pressures are exclusive of diluent, if any is present, and refer to the partial pressure of the feedstock as it relates to the oxygenate compound(s). Lower and upper extremes of pressure may adversely affect selectivity, conversion, coking rate, and/or reaction rate.

The result of the contact between the oxygenate feedstock, including the ammonia, and the selected catalyst will be formation of light olefins. In desirable embodiments the process may be continued for a period of time sufficient to produce the desired olefin products. The reaction time may vary from tenths of seconds to a number of hours. The reaction time is determined largely by the reaction temperature, the pressure, the catalyst selected, the weight hourly space velocity, the phase (liquid or vapor) and the selected process design characteristics.

A practical embodiment of a reactor system for the oxygenate conversion process is a circulating fluid bed reactor with continuous catalyst regeneration, similar to a modern fluid catalytic cracker. Fixed beds are generally not preferred for the process because oxygenate to olefin conversion is a highly exothermic process which requires several stages with intercoolers or other cooling devices. The reaction also tends to result in a large pressure drop, which is due to the production of low pressure, low density gases.

Because the catalyst must be regenerated frequently, the reactor should allow easy removal of a portion of the catalyst to a regenerator, where the catalyst is subjected to a regeneration medium, such as a gas comprising oxygen, for example air, to burn off coke from the catalyst, which restores the catalyst activity. The conditions of temperature, oxygen partial pressure, and residence time in the regenerator should be selected to achieve less than about 0.5 percent by weight (wt %) of coke on the regenerated catalyst. At least a portion of the regenerated catalyst is desirably returned to the reactor.

Using the various oxygenate feedstocks discussed above, particularly a feedstock containing methanol, the process of the invention is effective to convert the feedstock primarily into one or more olefin(s). The olefin(s) produced typically have from 2 to 30 carbon atoms, preferably 2 to 8 carbon atoms, more preferably 2 to 6 carbon atoms, still more preferably 2 to 4 carbons atoms, and most preferably are ethylene and/or propylene. In desirable embodiments the product will obtain the chief advantage of the present invention, which is that the ratio of ethylene to propylene in the product will be increased in comparison with the product resulting from an otherwise identical process that does not include the ammonia in the feed. Such will be encountered even where the combined ethylene plus propylene amount is the same. The resultant olefins may be separated from the oxygenate conversion product for sale or can be fed to a downstream process for converting the olefins to, for example, polymers.

EXAMPLES

Example 1

A methanol feed is prepared by adding a liquid solution of ammonia in an amount of 0.05 weight percent (wt %) to methanol. The liquid ammonia solution contains 30 wt % ammonia in 70 wt % of water. Using a continuous flow micro reactor system at ambient pressure, the methanol feed is combined with argon as a diluent. The methanol is flowed via a syringe pump at a flow rate of 0.003 grams per minute (g/min), and the argon is flowed at a rate of 20 milliliters per minute (mL/min) The feed thus contains approximately 10 percent by weight methanol and 90 percent by weight of argon. The reactor is an internal diameter ¼-inch by 6-inch stainless steel tube. An amount of catalyst, 200 milligrams (mg) of fresh, calcined SAPO-34 zeolite catalyst (U.S. mesh 20-50, 841-297 microns), is heated at 500° C. for 2 hours in argon to remove moisture, and is then positioned between quartz chips in the same size range in the reactor. The reaction temperature is controlled at 450° C. The methanol feed, containing the ammonia, is flowed through the reactor. Testing by gas chromatograph (GC) of the product is carried out and the results are recorded in Table 1.

Example 2

This Example 2 is carried out using the procedure and materials of Example 1, except increasing the amount of ammonia to 0.1 percent by weight. GC testing reveals the results recorded in Table 1.

Example 3

This Example 3 is carried out using the procedure and materials of Example 1, except increasing the amount of ammonia to 0.5 percent by weight. GC testing reveals the results recorded in Table 1.

Comparative Example A

This Comparative Example A is carried out using the procedure and materials of Example 1, except that no ammonia is included. GC testing reveals the results recorded in Table 1.

Comparative Example B

This Comparative Example B is carried out using the procedure and materials of Example 1, except 1.7 percent by weight water is used instead of the ammonia. GC testing reveals the results recorded in Table 1.

TABLE 1

| Constituent | Selectivity (100%)* | |
|---|---|---|
| | Ethylene | Propylene |
| Example 1 | 47.1 | 35.6 |
| Example 2 | 47.9 | 35.3 |
| Example 3 | 49.5 | 33.4 |
| Comparative Example A | 46.6 | 35.6 |
| Comparative Example B | 44.7 | 36.8 |

*Data are collected at 2.1 g-methanol/g-SAPO-34, 100% methanol conversion

What is claimed is:

1. A process for converting methanol to olefins comprising passing a methanol-containing feedstock over a catalyst capable of converting methanol to a product including ethylene and propylene, wherein from 0.05 to 0.5 weight percent of ammonia is included in the methanol-containing feedstock, such that the ratio of ethylene to propylene in the product is increased in comparison with the product of a process that is otherwise identical but lacks from 0.05 to 0.5 weight percent of ammonia in the methanol-containing feedstock.

2. The process of claim 1 wherein the conditions include a temperature from 200° C. to 700° C., a pressure from 0.01 megapascals to 2 megapascals, or both.

3. The process of claim 1 or 2, wherein the methanol-containing feedstock and the ammonia are in the vapor phase, liquid phase, or a mixed vapor/liquid phase.

4. The process of any of claims 1 to 3, wherein the ratio of ethylene to propylene is increased by at least 5 percent by weight.

5. The process of any of claims 1 to 4, wherein a molecular sieve catalyst selected from SAPO-34 and SAPO-18 is employed.

* * * * *